(12) United States Patent
Jin et al.

(10) Patent No.: US 9,795,390 B2
(45) Date of Patent: Oct. 24, 2017

(54) HEMOSTATIC CLIP (71) Applicant: MICO-TECH (NANJING) CO., LTD., Nanjing (CN)

(72) Inventors: Hongyan Jin, Nanjing (CN); Zhi Tang, Nanjing (CN); Mingqiao Fan, Nanjing (CN); Ran Song, Nanjing (CN)

(73) Assignee: MICRO-TECH (NANJING) CO., LTD, Nanjing (CN)

( * ) Notice: Subject to any disclaimer, the term of this patent is extended or adjusted under 35 U.S.C. 154(b) by 0 days.

(21) Appl. No.: 14/901,733

(22) PCT Filed: Jun. 30, 2014

(86) PCT No.: PCT/CN2014/081316
§ 371 (c)(1),
(2) Date: Dec. 29, 2015

(87) PCT Pub. No.: WO2015/176361
PCT Pub. Date: Nov. 26, 2015

(65) Prior Publication Data
US 2016/0367258 A1    Dec. 22, 2016

(30) Foreign Application Priority Data

May 23, 2014   (CN) .......................... 2014 1 0222753

(51) Int. Cl.
*A61B 17/122*        (2006.01)
*A61B 17/128*        (2006.01)
(Continued)

(52) U.S. Cl.
CPC ........ *A61B 17/122* (2013.01); *A61B 17/1285* (2013.01); *A61B 17/08* (2013.01);
(Continued)

(58) Field of Classification Search
CPC .............. A61B 17/122; A61B 17/1285; A61B 2017/12004; A61B 2017/00473; A61B 17/08
See application file for complete search history.

(56) References Cited

U.S. PATENT DOCUMENTS

| 5,382,253 A | * | 1/1995 | Hogendijk | ......... A61B 17/1285 |
| | | | | 227/901 |
| 5,391,180 A | * | 2/1995 | Tovey | ..................... A61B 1/32 |
| | | | | 600/224 |

(Continued)

FOREIGN PATENT DOCUMENTS

| CN | 101347361 A | 5/2011 |
| CN | 201578402 U | 1/2013 |

(Continued)

*Primary Examiner* — Katherine M Shi
*Assistant Examiner* — Michael Mendoza
(74) *Attorney, Agent, or Firm* — CBM Patent Consulting, LLC (57) ABSTRACT

A hemostatic clip comprises a clamping assembly and a clip base. The clamping assembly comprises a clip body and a steel wire buckle sequentially connected; a fixed hinge pin is arranged at the front end of the clip base, the clip body consists of two clamping arms, the tail ends of the two clamping arms are connected through a movable hinge pin, the middle part of each of the two clamping arms is provided with a chute, the fixed hinge pin penetrates through the chutes, and the two clamping arms reciprocate along the chutes so that the clip body can be opened and closed; a bent structure is arranged at the tail end of each chute; and when the clamping arms move to make the fixed hinge pin be located in the bent structures, the two clamping arms are located in the locked and closed position.

9 Claims, 4 Drawing Sheets (51) Int. Cl.
*A61B 17/08* (2006.01)
*A61B 17/00* (2006.01)
*A61B 17/12* (2006.01)

(52) U.S. Cl.
CPC ............... *A61B 2017/00473* (2013.01); *A61B 2017/12004* (2013.01)

(56) References Cited

U.S. PATENT DOCUMENTS

| | | | | |
|---|---|---|---|---|
| 5,431,675 A | * | 7/1995 | Nicholas | A61B 17/062 606/170 |
| 5,490,819 A | * | 2/1996 | Nicholas | A61B 1/32 600/201 |
| 5,514,157 A | * | 5/1996 | Nicholas | A61B 17/0218 600/201 |
| 5,766,184 A | * | 6/1998 | Matsuno | A61B 17/00234 604/15 |
| 8,545,534 B2 | * | 10/2013 | Ahlberg | A61B 17/282 606/207 |
| 8,771,293 B2 | * | 7/2014 | Surti | A61B 17/08 606/142 |
| 9,339,270 B2 | * | 5/2016 | Martinez | A61B 17/08 |
| 2007/0112422 A1 | | 5/2007 | Dehdashtian | |
| 2010/0057085 A1 | * | 3/2010 | Holcomb | A61B 18/1445 606/51 |
| 2012/0165863 A1 | * | 6/2012 | McLawhorn | A61B 17/08 606/207 |

FOREIGN PATENT DOCUMENTS

| | | |
|---|---|---|
| CN | 203828993 U | 9/2014 |
| EP | 1985261 A2 | 8/2012 |
| WO | WO94/20026 A1 | 10/2012 |
| WO | WO2006/069424 A2 | 10/2012 |

\* cited by examiner

HEMOSTATIC CLIP

This application is the U.S. national phase of International Application No. PCT/CN/2014/081316 Filed on 30 Jun. 2014 which designated the U.S. and claims priority to Chinese Application Nos. CN201410222753.7 filed on 23 May 2014, the entire contents of each of which are hereby incorporated by reference.

FIELD OF THE INVENTION

The present invention relates to medical equipment used inside human bodies, and particularly relates to a hemostatic clip capable of being conveniently separated and operated.

BACKGROUND OF THE INVENTION

In recent years, endoscopic hemostatic clips have become the most effective and most clinically valuable equipment for non-operational treatment of acute gastrointestinal tract hemorrhage of critical patients owing to the characteristics of low wound, high hemostatic speed, low re-bleeding rate, few complications, exact effect and the like. Hemostasis with a metal clip under an endoscope is one of the widely applicable hemostasis means, and the skilled metal clip operation for appropriate cases can effectively stop bleeding and prevent re-bleeding, reduce adverse response and greatly improve the safety and the cure rate of endoscopic therapy for gastrointestinal tract hemorrhage. The hemostatic mechanism of the metal hemostatic clip is the same as that of surgical vascular ligation or suture and is a physical and mechanical method, namely, a bleeding vessel and surrounding tissues thereof are ligated together by utilizing a mechanical force produced when the hemostatic clip is closed, so that the bleeding vessel is closed to block blood and fulfill the purpose of hemostasis; and the metal hemostatic clip is suitable for hemostatic therapy of non-variceal active bleeding and visible blood vessel stump lesions.

However, the existing hemostatic clip is inconvenient to place and fix, so a hemostatic clip convenient to use is urgently needed.

SUMMARY OF THE INVENTION

The aim of the present invention: the technical problem to be solved by the present invention is to provide a hemostatic clip for overcoming the defects of the prior art.

In order to solve the above technical problem, the present invention discloses a hemostatic clip, including a clamping assembly and a clip base, wherein the clamping assembly includes a clip body and a steel wire buckle which are sequentially connected; a fixed hinge pin is arranged at the front end of the clip base, the clip body is composed of two clamping arms, the tail ends of the two clamping arms are connected through a movable hinge pin, the middle part of each of the two clamping arms is provided with a chute, the fixed hinge pin penetrates through the chutes, and the two clamping arms reciprocate along the chutes so that the clip body can be opened and closed; a bent structure is arranged at the tail end of each chute; and when the clamping arms move to make the fixed hinge pin be located in the bent structures, the two clamping arms are located in the locked and closed position.

In the present invention, the steel wire buckle is wound on the movable hinge pin, and when the tension applied to the steel wire buckle reaches a predefined value (35-40N), the steel wire buckle is straightened and separated from the movable hinge pin; and after the steel wire buckle is separated from the movable hinge pin, the rear part of the clip body is fixed in the clip base.

In the present invention, a hook structure is arranged at the tail end of each of the two clamping arms, and the clip base is provided with protrusions matched with the hook structures; and when the two clamping arms are located in the locked and closed position, the hook structures at the tail ends of the two clamping arms are buckled on the protrusions. Thus, double insurance is formed, and the hemostatic clip is stable in the locked state and is not suddenly released again.

In the present invention, the engaged distal ends of the two clamping arms are matched in a serrated shape, so that two forceps heads are engaged synchronously to ensure the effectiveness after the clip is closed. After the engaged distal ends of the two clamping arms are closed, the end surfaces are spherical ones, so that the clip better passes through curves and protects the endoscopic tract.

In the present invention, the side walls of the two clamping arms are gradually widened from the distal ends to the proximal ends, so that the root strength of the clip can be improved, and the smoothness and the curve passing property of the clip are also ensured.

In the present invention, the clip base is sequentially connected with a transition cap, a fixed cap and a distal end spring tube to form an outer sleeve assembly, the clamping assembly includes a connector connected with the steel wire buckle, the connector is provided with an elastic pawl, more than two deformable buckles are arranged on the pawl, the clip base is partially nested with the transition cap, the mutually nested part is provided with a clamping groove capable of accommodating the buckles, and the buckles connect the clip base with the transition cap; and when the tension applied to the pawl reaches a preset value (20-30N), the buckles produce elastic deformation and are straightened, so that the buckles are separated from the clamping groove and the clip base is separated from the transition cap.

A transition cap insert is arranged at the tail end of the transition cap, so that an annular groove is formed in the outer wall of the transition cap; one end of the fixed cap is fixedly connected with the distal end spring tube, and the other end of the fixed cap is provided with an annular protrusion matched with the annular groove, so that the transition cap can rotate relative to the fixed cap.

In the present invention, the inside diameters of the fixed cap and the distal end spring tube are greater than the maximum outside diameters of the steel wire buckle, the connector and the pawl, so that the hemostatic clip in the present invention is different from a traditional device, and the separated steel wire buckle, connector and pawl can enter the distal end spring tube under the traction of an operation rope to reduce secondary harm to human bodies.

In the present invention, a spring tube transition piece is arranged in the distal end spring tube, the connector is connected with the operation rope, and the spring tube transition piece is provided with a through hole through which only the operation rope passes, so that the spring tube transition piece forms a stop.

In the present invention, holes, through which the movable hinge pin passes, of the clamping arms are kidney-shaped, so that the buckles are easily staggered and reduced to enter the clip base hole and can be bounced off again to clamp the clip, the closing resistance can be effectively reduced, the clamping force can be improved, and the clip can complete clamping and closure without dropping off.

In the present invention, the chute has radian. The chute is designed in an arc or straight shape, so that the clip moves smoothly and achieves the designed opening size.

Beneficial effects: the hemostatic clip of the present invention is simple and convenient to operate, and can rotate conveniently inside the human body according to the requirement of various angles; meanwhile, after the hemostatic clip is positioned successfully, it can be released through the operation rope, so that the hemostatic clip body is left inside the human body.

BRIEF DESCRIPTION OF THE DRAWINGS

The present invention will be further specifically described below in combination with the accompanying drawings and the specific embodiments, and the above-mentioned and other advantages of the present invention will be clearer.

DETAILED DESCRIPTION OF THE EMBODIMENTS

The present invention discloses a hemostatic clip, including a clamping assembly and a clip base, wherein the clamping assembly includes a clip body and a steel wire buckle which are sequentially connected; a fixed hinge pin is arranged at the front end of the clip base, the clip body is composed of two clamping arms, the tail ends of the two clamping arms are connected through a movable hinge pin, the middle part of each of the two clamping arms is provided with a chute, the fixed hinge pin penetrates through the chutes, and the two clamping arms reciprocate along the chutes so that the clip body can be opened and closed; a bent structure is arranged at the tail end of each chute; and when the clamping arms move to make the fixed hinge pin be located in the bent structures, the two clamping arms are located in the locked and closed position.

The steel wire buckle is wound on the movable hinge pin, and when the tension applied to the steel wire buckle reaches a predefined value, the steel wire buckle is straightened and separated from the movable hinge pin; and after the steel wire buckle is separated from the movable hinge pin, the rear part of the clip body is fixed in the clip base.

A hook structure is arranged at the tail end of each of the two clamping arms, and the clip base is provided with protrusions matched with the hook structures; and when the two clamping arms are located in the locked and closed position, the hook structures at the tail ends of the two clamping arms are buckled on the protrusions.

The engaged distal ends of the two clamping arms are matched in a serrated shape. After the engaged distal ends of the two clamping arms are closed, the end surfaces are spherical ones. The side walls of the two clamping arms are gradually widened from the distal ends to the proximal ends. The proximal ends approach an operator, while the distal ends are far from the operator and approach a target lesion.

The clip base is sequentially connected with a transition cap, a fixed cap and a distal end spring tube to form an outer sleeve assembly, the clamping assembly includes a connector connected with the steel wire buckle, the connector is provided with an elastic pawl, more than two deformable buckles are arranged on the pawl, the clip base is partially nested with the transition cap, the mutually nested part is provided with a clamping groove capable of accommodating the buckles, and the buckles connect the clip base with the transition cap; and when the tension applied to the pawl reaches a preset value, the buckles produce elastic deformation and are straightened, so that the buckles are separated from the clamping groove and the clip base is separated from the transition cap.

A transition cap insert is arranged at the tail end of the transition cap, so that an annular groove is formed in the outer wall of the transition cap; one end of the fixed cap is fixedly connected with the distal end spring tube, and the other end of the fixed cap is provided with an annular protrusion matched with the annular groove, so that the transition cap can rotate relative to the fixed cap.

The inside diameters of the fixed cap and the distal end spring tube are greater than the maximum outside diameters of the steel wire buckle, the connector and the pawl.

A spring tube transition piece is arranged in the distal end spring tube, the connector is connected with an operation rope, and the spring tube transition piece is provided with a through hole through which only the operation rope passes.

Holes, through which the movable hinge pin passes, of the clamping arms are kidney-shaped.

The chutes have radian.

EMBODIMENTS

Figure 1:
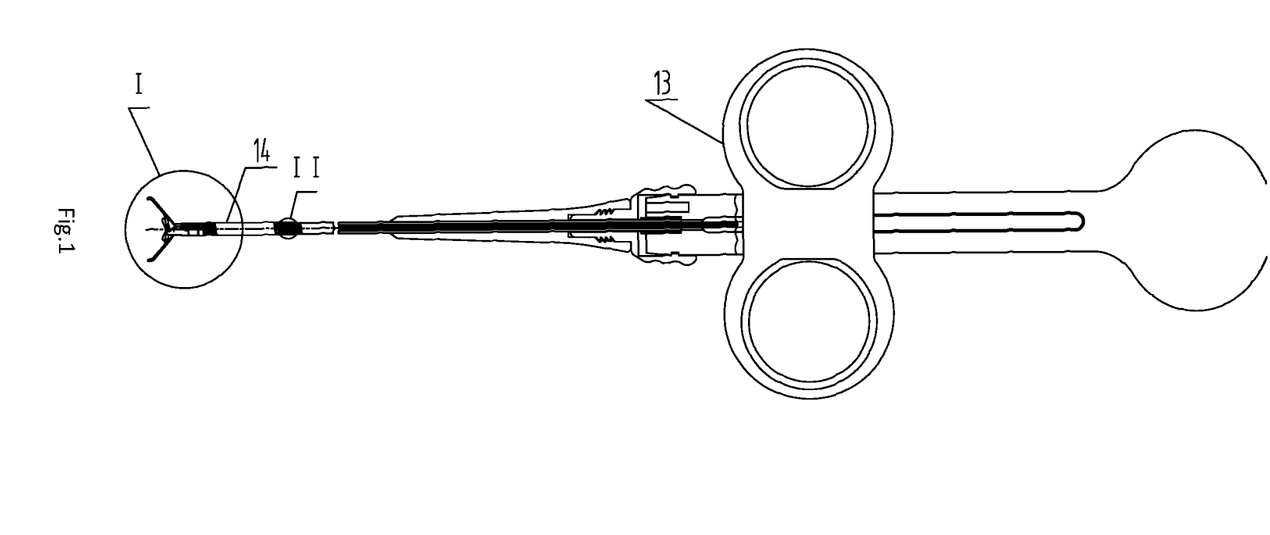
FIG. 1 is a schematic diagram of an overall structure of the present invention.
Figure 2:
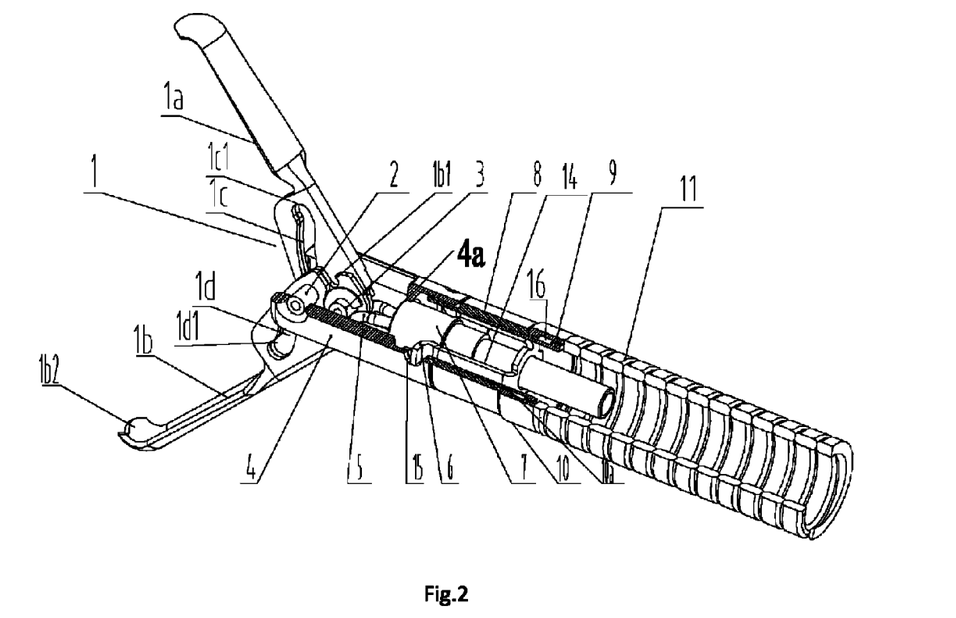
FIG. 2 is a partial enlarged diagram of part I in FIG. 1.
Figure 6:
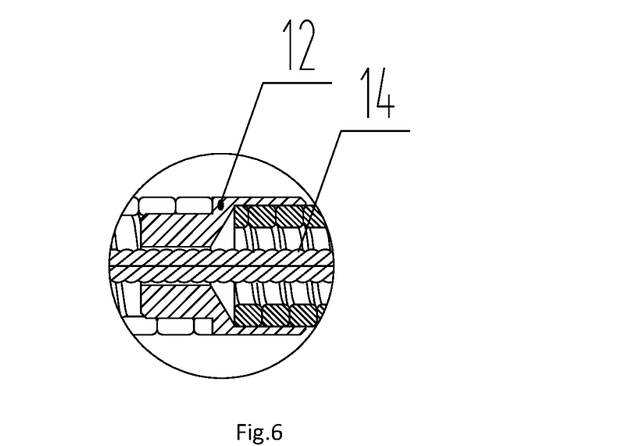
FIG. 6 is a partial enlarged diagram of part II in FIG. 1.
Figure 7:
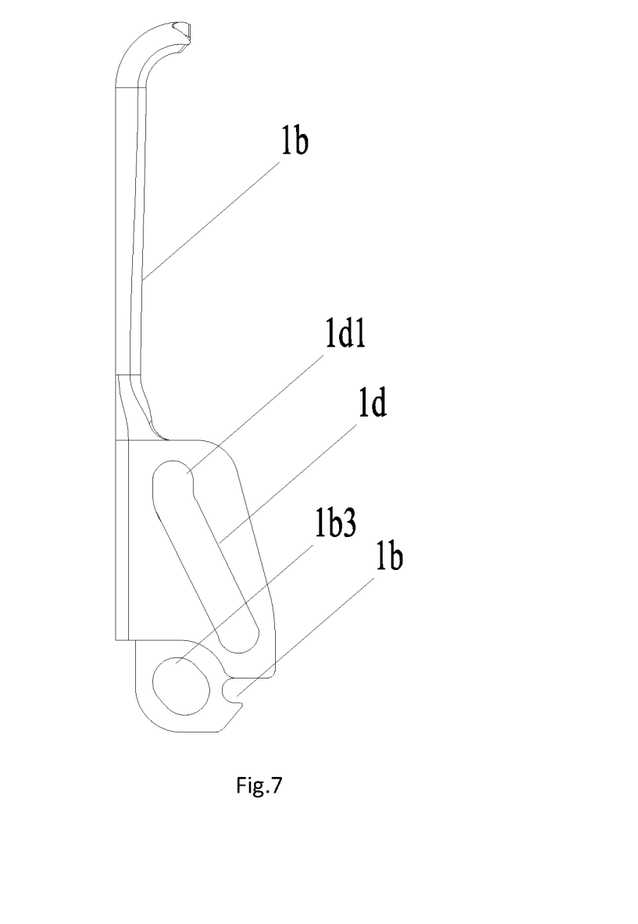
FIG. 7 is a structural schematic diagram of a clamping arm.

As shown in FIG. 1 and FIG. 2, the present invention discloses a hemostatic clip, including an outer sleeve assembly and a clamping assembly positioned inside the outer sleeve assembly, wherein the outer sleeve assembly includes a clip base 4, a transition cap 8, a fixed cap 10 and a distal end spring tube 11 which are sequentially connected; the clamping assembly includes a clip body 1, a steel wire buckle 5, a connector 7 and an operation rope 14 for connecting an operation handle 13 which are connected in sequence; and a fixed hinge pin 2 is arranged at the front end of the clip base, the clip body is composed of two clamping arms 1a and 1b, the tail ends of the two clamping arms are connected through a movable hinge pin 3, the middle part of each of the two clamping arms is provided with a chute 1c or 1d, and the engaged distal ends of the two clamping arms are matched in a serrated shape 1b2. As shown in FIG. 7, bent structures 1c1 and 1d1 are arranged at the tail ends of the chutes 1c and 1d, the fixed hinge pin penetrates through the chutes 1c and 1d, and the two clamping arms reciprocate along the chutes so that the clip body can be opened and closed; the steel wire buckle 5 is wound on the movable hinge pin 3, and when the tension applied to the steel wire buckle reaches a predefined value, the steel wire buckle is straightened and separated from the movable hinge pin; and after the steel wire buckle is separated from the movable hinge pin, the clip body is fixed in the clip base 4. The connector 7 is provided with an elastic pawl 14, buckles 6 are arranged on the pawl, the clip base 4 and the transition cap 8 have a mutually nested and superposed part, the mutually nested part is provided with a clamping groove 15 capable of accommodating the buckles 6, and the buckles connect the clip base 4 with the transition cap 8; when the tension applied to the buckles 6 reaches a preset value, the buckles 6 produce elastic deformation and are straightened, so that the buckles are separated from the clamping groove and the clip base is separated from the transition cap; a transition cap insert 9 is arranged at the tail end of the transition cap 8, so that an annular groove 16 is formed in the outer wall of the transition cap; one end of the fixed cap 10 is fixedly connected with the distal end spring tube 11, and the other end of the fixed cap 10 is provided with an annular protrusion 10a matched with the annular groove, so that the transition cap can rotate relative to the fixed cap. The inside diameters of the fixed cap and the distal end spring tube are greater than the maximum outside diameters of the steel wire buckle, the connector and the pawl. As shown in FIG. 6, a spring tube transition piece 12 is arranged in the distal end spring tube, and the spring tube transition piece is provided with a through hole through which only the operation rope 14 passes. As shown in FIG. 7, a hole, through which the movable hinge pin passes, of the clamping arm is kidney-shaped 1b3.

FIG. 2 shows a splayed state of the two clamping arms 1a and 1b, and at the moment, the hemostatic clip can be aligned with a human part which needs to be clamped for hemostasis. The operation rope 14 can be rotated as required to drive the hemostatic clip body to rotate.

Figure 3:
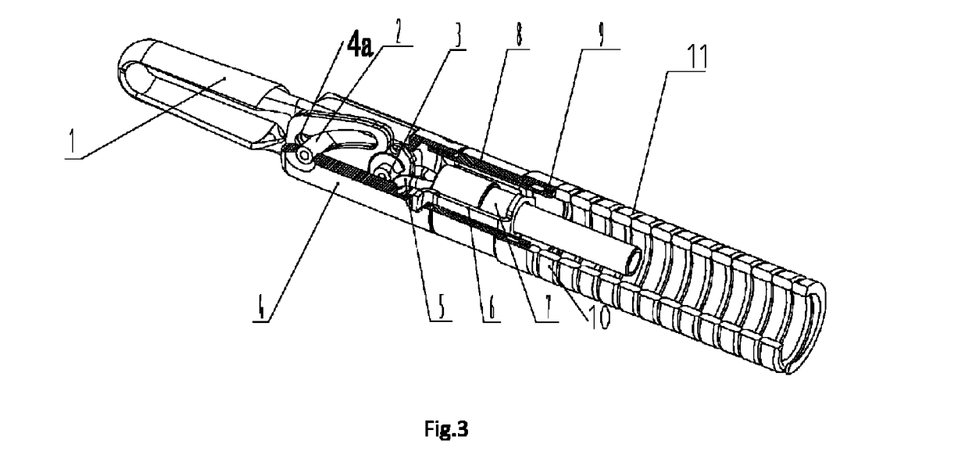
FIG. 3 is a schematic diagram of a first change state in FIG. 2.

As shown in FIG. 3, after the hemostatic part is found (in the present invention, the hemostatic clip body is forward, and the operation rope is backward), the operation rope 14 is pulled backwards, and the two clamping arms 1a and 1b retreat along a track formed by the chutes 1c and 1d and the fixed hinge pin 2 and are closed. The bent structures 1c1 and 1d1 are arranged at the tail ends of the chutes 1c and 1d, and when the clamping arms move so that the fixed hinge pin is located in the bent structures, the two clamping arms 1a and 1b are closed when moving backwards, and the tail ends of the chutes 1c and 1d are locked. Meanwhile, hook structures 1b1 are arranged at the tail ends of the two clamping arms, the clip base is provided with protrusions 4a matched with the hook structures; and when the two clamping arms are located in the locked and closed position, the hook structures at the tail ends of the two clamping arms are buckled on the protrusions. At the position, the clamping arms 1a and 1b do not splay again.

Figure 4:
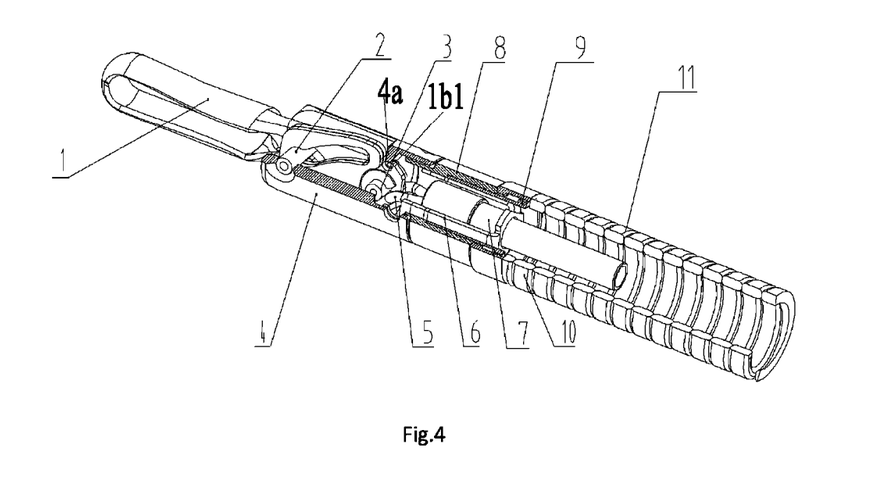
FIG. 4 is a schematic diagram of a second change state in FIG. 2.

As shown in FIG. 4, the operation rope 14 is continuously pulled backwards, and when the tension applied to the buckles 6 reaches a preset value (20-30N), the buckles 6 produce elastic deformation and are straightened, so that the buckles are separated from the clamping groove and the clip base is separated from the transition cap.

Figure 5:
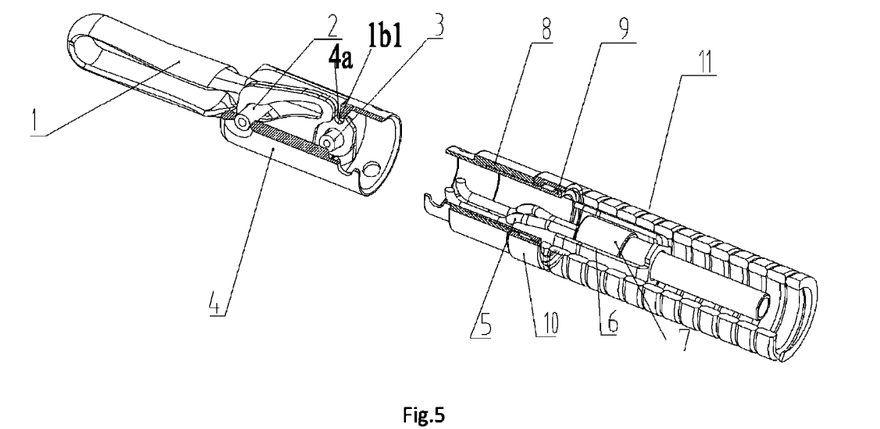
FIG. 5 is a schematic diagram of a third change state in FIG. 2.

As shown in FIG. 5, the operation rope 14 is continuously pulled backwards, and when the tension applied to the steel wire buckle 5 reaches a predefined value (35-40N), the steel wire buckle 5 is deformed, straightened and separated from the movable hinge pin.

In this embodiment, the side walls of the two clamping arms are gradually widened from the distal ends to the proximal ends.

In this embodiment, the chutes have radian.

When the hemostatic clip is used, the hemostatic clip body is delivered to the specified lesion position under the auxiliary monitoring effect of an endoscope, a conductive plug at the handle is connected to a high-frequency power supply, a slider retreats, forceps heads are closed, and then the hemostatic clip can be used as a high-frequency incision knife for marking and incising lesion tissues; and if bleeding happens in operation, the slider at the handle can be propelled, the forceps head is opened, meanwhile, a mandrel is rotated to drive the forceps head to rotate, and then the hemostatic clip can be used as hemostatic forceps for hemostasis. The hemostatic clip can clip out the incised lesion tissues after the operation.

What is claimed is:

1. A hemostatic clip, comprising a clamping assembly and a clip base, wherein the clamping assembly comprises a clip body and a steel wire buckle which are sequentially connected;

a fixed hinge pin is arranged at the front end of the clip base, the clip body is composed of two clamping arms, the tail ends of the two clamping arms are connected through a movable hinge pin, the middle part of each of the two clamping arms is provided with a chute, the fixed hinge pin penetrates through the chutes, and the two clamping arms reciprocate along the chutes so that the clip body can be opened and closed; a bent structure is arranged at the tail end of each chute; and when the clamping arms move to make the fixed hinge pin be located in the bent structures, the two clamping arms are located in locked and closed position; wherein the steel wire buckle is wound on the movable hinge pin, and when the tension applied to the steel wire buckle reaches a predefined value, the steel wire buckle is straightened and separated from the movable hinge pin; and after the steel wire buckle is separated from the movable hinge pin, the rear part of the clip body is fixed in the clip base.

2. The hemostatic clip of claim 1, wherein a hook structure is arranged at the tail end of each of the two clamping arms, and the clip base is provided with protrusions matched with the hook structures; and when the two clamping arms are located in the locked and closed position, the hook structures at the tail ends of the two clamping arms are buckled on the protrusions.

3. The hemostatic clip of claim 1, wherein the engaged distal ends of the two clamping arms are matched in a serrated shape.

4. The hemostatic clip of claim 1, wherein the side walls of the two clamping arms are gradually widened from the distal ends to the proximal ends.

5. The hemostatic clip of claim 1, wherein the clip base is sequentially connected with a transition cap, a fixed cap and a distal end spring tube to form an outer sleeve assembly, the clamping assembly comprises a connector connected with the steel wire buckle, the connector is provided with an elastic pawl, more than two deformable buckles are arranged on the pawl, the clip base is partially nested with the transition cap, the mutually nested part is provided with a clamping groove capable of accommodating the buckles, and the buckles connect the clip base with the transition cap; and when the tension applied to the pawl reaches a preset value, the buckles produce elastic deformation and are straightened, so that the buckles are separated from the clamping groove and the clip base is separated from the transition cap;

a transition cap insert is arranged at the tail end of the transition cap, so that an annular groove is formed in the outer wall of the transition cap; one end of the fixed cap is fixedly connected with the distal end spring tube, and the other end of the fixed cap is provided with an annular protrusion matched with the annular groove, so that the transition cap can rotate relative to the fixed cap.

6. The hemostatic clip of claim 5, wherein the inside diameters of the fixed cap and the distal end spring tube are greater than the maximum outside diameters of the steel wire buckle, the connector and the pawl.

7. The hemostatic clip of claim 5, wherein a spring tube transition piece is arranged in the distal end spring tube, the connector is connected with an operation rope, and the spring tube transition piece is provided with a through hole through which only the operation rope passes.

8. The hemostatic clip of claim 1, wherein holes, through which the movable hinge pin passes, of the clamping arms are kidney-shaped.

9. The hemostatic clip of claim 1, wherein the chutes have radian.

* * * * *

UNITED STATES PATENT AND TRADEMARK OFFICE
CERTIFICATE OF CORRECTION

PATENT NO. : 9,795,390 B2  
APPLICATION NO. : 14/901733  
DATED : October 24, 2017  
INVENTOR(S) : Jin et al.

Page 1 of 1

It is certified that error appears in the above-identified patent and that said Letters Patent is hereby corrected as shown below:

On the Title Page

Item (71) Applicant change to read:  
MICRO-TECH (NANJING) CO., LTD, NANJING (CN)

Signed and Sealed this  
Fifth Day of December, 2017

Joseph Matal  
*Performing the Functions and Duties of the*  
*Under Secretary of Commerce for Intellectual Property and*  
*Director of the United States Patent and Trademark Office*